(12) United States Patent
Yamaoka et al.

(10) Patent No.: US 7,201,042 B2
(45) Date of Patent: Apr. 10, 2007

(54) MEASURING INSTRUMENT PROVIDED WITH SOLID COMPONENT CONCENTRATING MEANS

(75) Inventors: Hideaki Yamaoka, Kyoto (JP); Koji Katsuki, Kyoto (JP)

(73) Assignee: Arkray, Inc., Kyoto (JP)

( * ) Notice: Subject to any disclaimer, the term of this patent is extended or adjusted under 35 U.S.C. 154(b) by 0 days.

(21) Appl. No.: 10/533,602

(22) PCT Filed: Oct. 30, 2003

(86) PCT No.: PCT/JP03/13963

§ 371 (c)(1),
(2), (4) Date: Apr. 29, 2005

(87) PCT Pub. No.: WO2004/040289

PCT Pub. Date: May 13, 2004

(65) Prior Publication Data

US 2006/0042361 A1    Mar. 2, 2006

(30) Foreign Application Priority Data

Nov. 1, 2002  (JP)  .............................. 2002-320295

(51) Int. Cl.
*G01N 15/06*   (2006.01)
*G01N 1/00*    (2006.01)

(52) U.S. Cl. .................. 73/61.71; 73/64.56; 324/71.4; 204/403.06

(58) Field of Classification Search ........... 204/403.11, 204/403.01, 403.06; 73/61.71, 64.56, 865.5; 324/71.4, 71.1, 449

See application file for complete search history.

(56) References Cited

U.S. PATENT DOCUMENTS 3,238,452 A * 3/1966 Schmitt et al. ............. 324/666

4,897,173 A * 1/1990 Nankai et al. ......... 204/403.05

(Continued)

FOREIGN PATENT DOCUMENTS

EP    1 235 068    8/2002

(Continued)

OTHER PUBLICATIONS

Hanning, I. et al. "Improved Blood Compatibility at a Glucose Enzyme Electrode Used for Extracorporeal Monitoring", Analyticall Letters, 19(384), 461-478 (1986).*

(Continued)

*Primary Examiner*—Michael Cygan
(74) *Attorney, Agent, or Firm*—Hamre, Schumann, Mueller & Larson, P.C.

(57) ABSTRACT

The present invention relates to a measuring instrument (1) comprising a channel (60) for moving a sample liquid (BL) containing a solid component (B1) and providing a liquid reaction field and first and second electrodes (31, 32) which are used to apply voltage to the liquid reaction field. The first electrode (31) has an electron transfer interface (31*a*) for transferring electrons between it and the liquid reaction field when voltage is applied to the liquid reaction field via the first and second electrodes (31, 32). The measuring instrument (1) comprises concentrating means (51) for increasing the concentration of solid components at portions thereof which contact the electron transfer interface (31*a*) in the liquid reaction field. The concentrating means (51) preferably comprises a water-absorbing layer containing an absorbent polymer material.

16 Claims, 8 Drawing Sheets

U.S. PATENT DOCUMENTS

| | | |
|---|---|---|
| 5,681,529 A | 10/1997 | Taguchi et al. |
| 5,958,199 A | 9/1999 | Miyamoto et al. |
| 6,391,265 B1 | 5/2002 | Buechler et al. |
| 6,719,887 B2 | 4/2004 | Hasegawa et al. |
| 6,723,371 B2 * | 4/2004 | Chih-hui .................. 427/2.13 |
| 6,761,816 B1 * | 7/2004 | Blackburn et al. ....... 205/777.5 |

FOREIGN PATENT DOCUMENTS

| | | |
|---|---|---|
| JP | 63058149 A * | 3/1988 |
| JP | 03170854 * | 7/1991 |
| JP | 6-130023 | 5/1994 |
| JP | 8-114539 | 5/1996 |
| JP | 9-243591 | 9/1997 |
| JP | 2000-81407 | 3/2000 |
| JP | 2000-338076 | 12/2000 |
| JP | 2002-508698 | 3/2002 |
| JP | 2002-189014 | 7/2002 |
| JP | 2002-202283 | 7/2002 |
| JP | 2002-535615 | 10/2002 |
| JP | 2002-535616 | 10/2002 |
| WO | WO 00/42424 | 7/2000 |
| WO | WO 00/42422 | 7/2001 |

OTHER PUBLICATIONS

Hanning et al. "Improved blood compatibility at glucose enzyme electrode used for extracorporeal monitoring", *Analytical Letters*, vol. 19, No. 3/4, pp. 461-478 (1986).

* cited by examiner

Time Course of Response Values (Example 1)

FIG. 12

Time Course of Response Values (Comparative Example 1)

FIG.13

Effect of Hct (Example 1)

FIG.14

Effect of Hct (Comparative Example 1)

MEASURING INSTRUMENT PROVIDED WITH SOLID COMPONENT CONCENTRATING MEANS

TECHNICAL FIELD

The present invention relates to a measuring instrument to be used for measuring the concentration of a specific component (such as glucose or cholesterol) in a sample liquid such as blood.

BACKGROUND ART

Some methods of measuring the concentration of a specific component in a sample liquid employ electrochemical techniques for example. In these methods, a reaction system is formed from a sample liquid, an oxidoreductase and an electron transporter for example, voltage is applied to this reaction system using electrodes, and the concentration of the specific component is computed based on the resulting response current. Such a reaction system is formed for example on a biosensor provided with a reagent part comprising an oxidoreductase and an electron transporter. Because an oxidation-reduction reaction occurs between the specific component and the electron transporter in the reaction system due to the catalytic effect of the oxidoreductase, the amount of the electron transporter which becomes reduced (or oxidized) reflects the concentration of the specific component. Response current is obtained in correlation with the amount of electron movement occurring in the reaction system. Consequently, the accuracy of concentration measurement is greatly affected by the accuracy of measurement of response current.

In such methods, when blood (blood containing blood cells) is used as a sample liquid, electron movement between the electrode and the electron transporter is impeded by blood cells present on the surface of the electrode. As a result, the measured response current is reduced as the number of blood cells increases, producing measurement errors. Moreover, if the proportion of blood cells in the blood (hematocrit value) is different the measured response current will be different even if the glucose concentration is the same.

To solve these problems, methods have been proposed of separating blood cells from blood in the measuring instrument. Methods of separating blood cells include for example a method of providing a separation membrane in that part of the measuring instrument where blood or other sample liquid is introduced (see for example JP-A 8-114539 and JP-A 2002-508698), and a method of covering the surface of the electrode with a polymer membrane (see for example JP-A 6-130023, JP-A 9-243591 and JP-A 2000-338076).

However, because in methods which filter blood cells in the measuring instrument the plasma component must pass through the separation membrane it takes a long time for the plasma to reach the surface of the electrode, prolonging the measurement time. This problem can be solved by securing a large quantity of whole blood to be used, but this places a heavy burden of blood collection on the user.

DISCLOSURE OF THE INVENTION

It is an object of the present invention to control the effect of the solid component in the sample liquid and precisely measure concentration with a small amount of sample liquid while keeping the measurement time short.

In the present invention a measuring instrument is provided which is an analytical instrument comprising a channel for moving a sample liquid containing a solid component and for providing a liquid reaction field and a first and second electrode which are used to apply voltage to the liquid reaction field, wherein the first electrode has an electron transfer interface for providing electrons to the liquid reaction field or receiving electrons from the reaction field when voltage is applied to the liquid reaction field via the first and second electrodes, and which is provided with concentration means for increasing the concentration of solid components in that part which contacts the electron transfer interface in the liquid reaction field.

The concentration means comprises for example a water-absorbing layer containing an absorbent polymer material. The absorbent polymer material must be capable of absorbing enough liquid component to achieve the object of the present invention, and the amount of water absorbed must not be such as to affect the measurement results. Consequently, it is desirable to use an absorbent polymer material having a water absorption power of 10 to 500 g/g.

The measuring instrument includes for example a substrate on which are formed the first and second electrodes with a cover laid over the substrate.

The water-absorbing layer is formed as a film on at least a part of the cover which faces the electron transfer interface for example. In this case, the water-absorbing layer is preferably formed so that its dimension in the direction of thickness of the substrate without water absorption and with water absorption is $\frac{1}{30}$ to $\frac{1}{10}$ and $\frac{1}{5}$ to $\frac{3}{5}$, respectively, of the dimension in the direction of thickness of the channel. The water-absorbing layer can also be made water-soluble.

The water-absorbing layer may also be formed across all or most of the length of the channel. Such a water-absorbing layer can be the cover if the cover contains an absorbent material.

The water-absorbing layer may comprise powder of an absorbent polymer material supported on the cover. The weight average grain size of the powder without water absorption is 100 to 1000 μm for example. This is because if the average grain size in unsuitably small it is difficult to form the water-absorbing layer so that it cannot absorb enough water to achieve the object, while if the average grain size is unsuitably large it will impede the flow of water in the channel more than necessary.

The water-absorbing layer can also be placed downstream in the flow of sample liquid from the electron transfer interface in the channel. This water-absorbing layer is placed for example on either the substrate or the cover. In this case the dimension of the water-absorbing layer in the direction of flow of the sample liquid is preferably ¼ to ½ of the distance from the channel inlet to the furthest downstream point of the electron transfer interface in the direction of flow of the sample liquid so that the solid component can be concentrated as intended. For the same reasons it is desirable that during water absorption the thickness of the part having the formed water-absorbing layer be 0 to 15 μm.

The water-absorbing layer can also be formed so as to have a part formed in at least one of a location upstream from and adjacent to the electron transfer interface and a location downstream from and adjacent to the electron transfer interface. In this case, the water-absorbing layer is preferably formed so as to have both a part formed in a location upstream from and adjacent to the electron transfer interface and a part downstream from and adjacent to the electron transfer interface, and it is formed for example so as to surround the electron transfer interface.

The concentrating means can also be provided downstream in the channel from the electron transfer interface in the direction of movement of the sample liquid and can be formed by a absorption-resistant dam to impede the movement of the solid components.

The dam is formed so that the thickness of the channel where the dam part is formed is 5 to 15 μm for example so as to concentrate the solid components as intended.

The same liquid which is measured in the measuring instrument of the present instrument may classically be blood containing blood cells as the solid component. The measuring instrument of the present invention can be used for a wide range of sample liquids containing solid components, and the sample liquid which is measured is not limited to blood.

BEST MODE FOR CARRYING OUT THE INVENTION

Embodiments 1 through 5 of the present invention are explained in detail below with reference to the drawings.

First, the first embodiment of the present invention is explained using blood sugar measurement as an example with reference to FIGS. 1 through 5.

Figure 1:
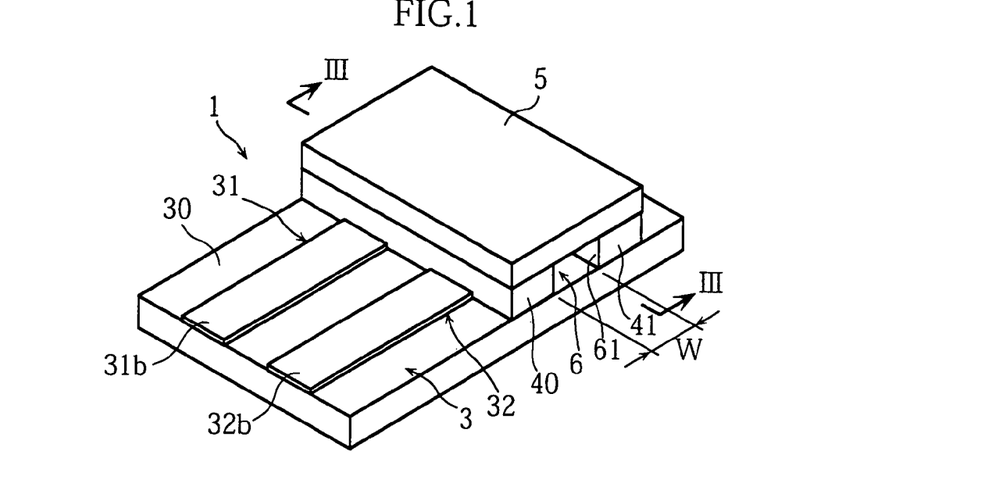
FIG. 1 is a perspective view of a biosensor according to a first embodiment of the present invention.
Figure 2:
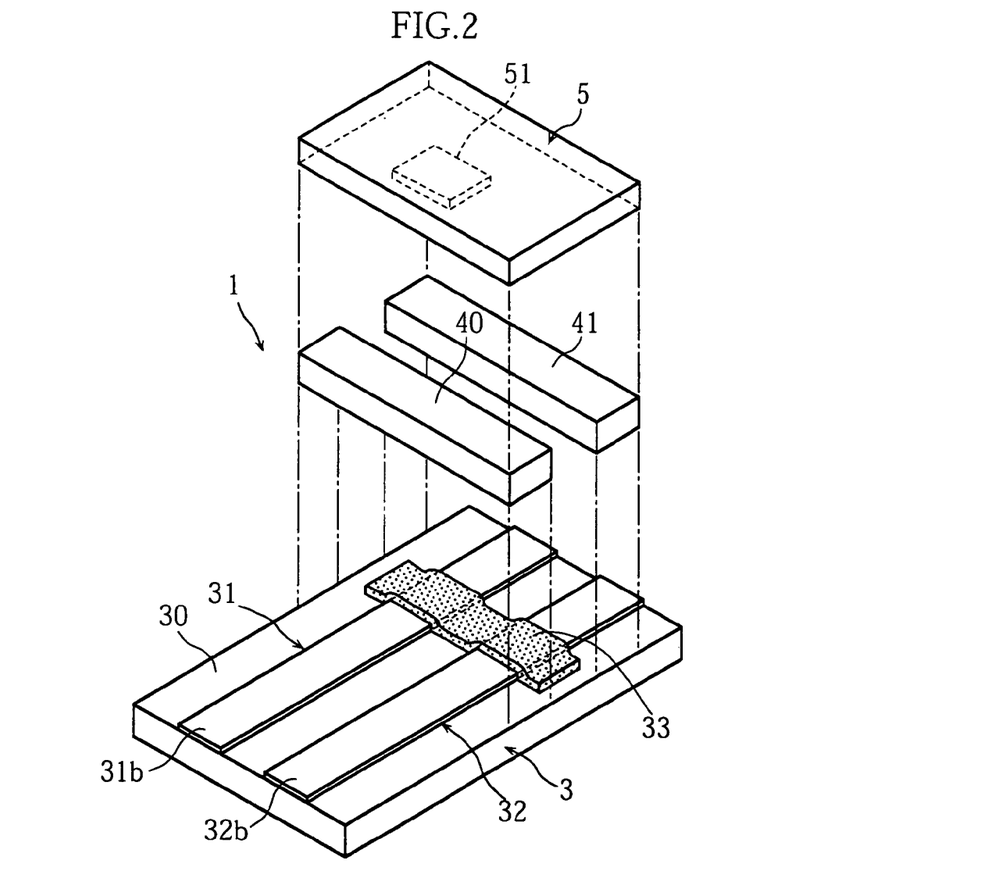
FIG. 2 is an exploded perspective view of the biosensor shown in FIG. 1.
Figure 5:
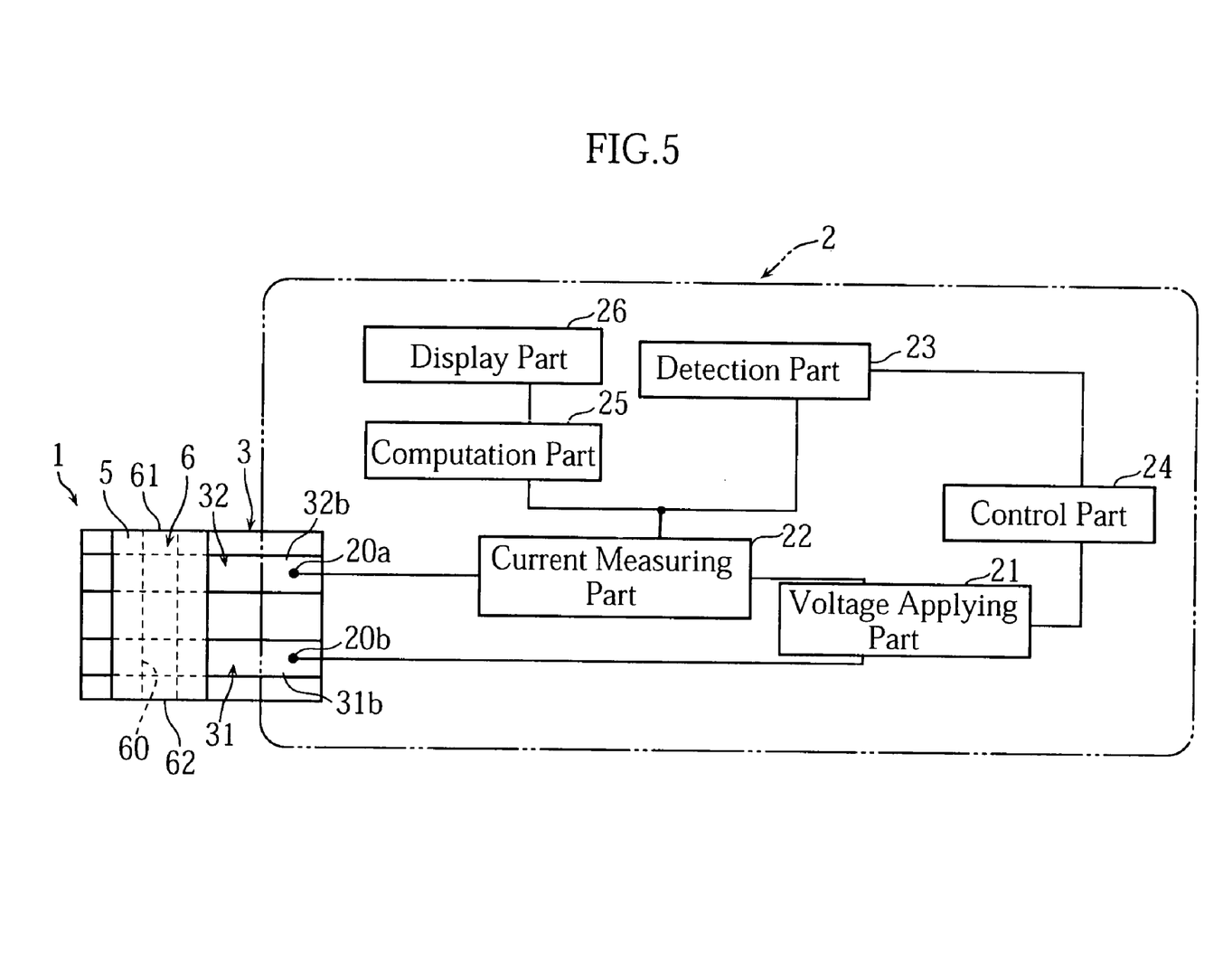
FIG. 5 is a block diagram showing the biosensor shown in FIG. 1 mounted on a concentration measuring system.

The biosensor 1 shown in FIGS. 1 and 2 is used to measure glucose concentrations in blood, and is used mounted on concentration measuring system 2 (see FIG. 5). This biosensor 1 includes cover 5 laid over rectangular substrate 3 with a pair of spacers 40 and 41 in between, and as shown in FIG. 3, capillary 6 is formed by these elements 3, 40, 41 and 5.

Capillary 6 moves blood by means of capillary action, and has internal channel 60 for holding the blood. This internal channel 60 extends in the short direction of substrate 3, and communicates with the outside via end openings 61 and 62. End opening 61 is used to introduce blood into internal channel 60, and when blood is moved through internal channel 60 end openings 62 is used to exhaust gas from internal channel 60.

Figure 3:
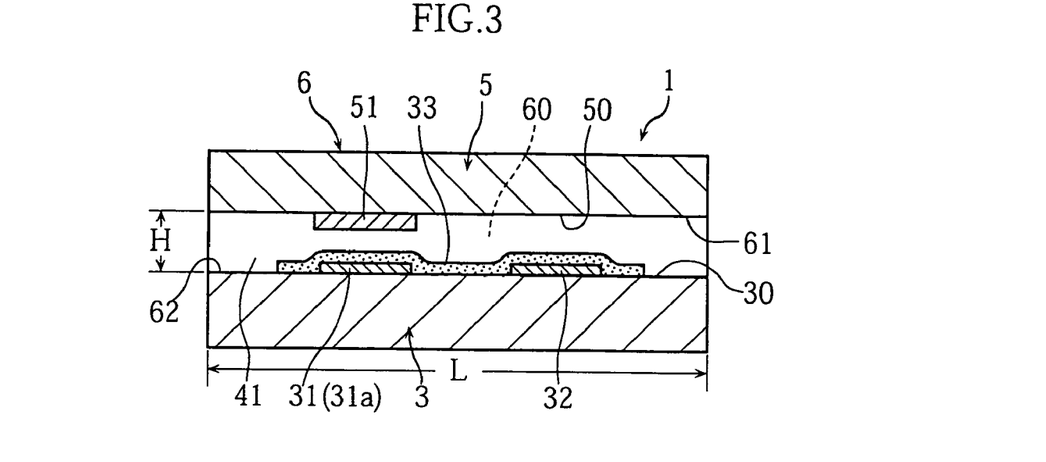
FIG. 3 is a cross-section along line III—III in FIG. 1.

As shown in FIGS. 1 through 3, the pair of spacers 40 and 41 serve to join cover 5 to substrate 3 and to determine the dimensions of internal channel 60 of capillary 6. The pair of spacers 40 and 41 extend in the short direction of substrate 3, and are arranged with a gap between them in the long direction of substrate 3.

Working electrode 31 and counter electrode 32 are formed extending in the long direction of substrate 3 on upper surface 30 of substrate 3. Reagent site 33 is also provided on upper surface 30 of substrate 3 so as to successively transect both working electrode 31 and counter electrode 32. The part of working electrode 31 which contacts reagent site 33 comprises electron transfer interface 31a.

Reagent site 33 is formed as a solid which comprises an oxidoreductase and an electron transporter. Glucose oxidase or glucose dehydrogenase for example can be used as the oxidoreductase. The electron transporter is oxidized or reduced by application of voltage and reactions, and in blood sugar measurement potassium ferricyanide for example is used as the electron transporter. In this embodiment, the electron transporter is included in its oxidized form before the blood is supplied.

As shown in FIGS. 2 and 3, water-absorbing layer 51 is formed on one side 50 of cover 5. This water-absorbing layer 51 is formed on one side 50 of cover 5 so as to face electron transfer interface 31a, which is located in internal channel 60 on working electrode 31. This water-absorbing layer 51 can be formed by affixing a water-absorbing sheet comprising an absorbent polymer material to cover 5. This water-absorbing layer 51 is formed so that its thickness is for example 1/30 to 1/10 of the height (H) of internal channel 60 without water absorption, and so that its thickness with water absorption is 1/5 to 3/5 the height (H) of internal channel 60.

A material with water absorption power of 10 to 500 g/g for example is used as the absorbent polymer material. Specific examples of the absorbent polymer material include crosslinked acrylate polymers, crosslinked vinyl alcohol-acrylate copolymers, crosslinked maleic anhydride grafted polyvinyl alcohol, crosslinked isobutylene-maleic anhydride copolymer, carboxymethylcellulose crosslinked with alkali salts, crosslinked partially neutralized polyacrylic acid and the like. Water absorbing layer 51 may be entirely formed of an absorbent polymer material, or it may be formed as a layer which is a mixture of an absorbent polymer material and a non-absorbent polymer material. Water-absorbing layer 51 can be formed by first applying a solution of an absorbent polymer material dissolved in a solvent to cover 5 and then drying it.

As shown in FIG. 5, concentration measuring system 2 includes first and second terminals 20a and 20b, voltage applying part 21, current measuring part 22, detection part 23, control part 24, computation part 25 and display part 26.

First and second terminals 20a and 20b are provided for contact with terminals 31b and 32b of working electrode 31 and counter electrode 32 in biosensor 1 when biosensor 1 is mounted on concentration measuring system 2.

Voltage applying part 21 is for applying a voltage between working electrode 31 and counter electrode 32 of biosensor 1 via first and second terminals 20a and 20b. Voltage applying part 21 is electrically connected to first and second terminals 20a and 20b. Voltage applying part 21 includes for example a direct current power source such as a dry battery or charger.

Current measuring part 22 measures the current when a voltage is applied by means of voltage applying part 21 between terminals 31b and 32b of working electrode 31 and counter electrode 32.

Detection part 23 detects based on the current measured by current measuring part 22 whether or not a sample liquid has been supplied to reagent part 33 (see FIGS. 1 through 3) after biosensor 1 has been mounted on concentration measuring system 2.

Control part 24 controls voltage applying part 21 and selects whether a voltage is applied or not between working electrode 31 and counter electrode 32.

Computation part 25 computes the blood sugar concentration according to the current measured by current measuring part 22. Computation part 25 is designed so as to compute the blood sugar concentration by amperometric means for example.

Detection part 23, control part 24 and computation part 25 may include multiple memories (such as ROM or RAM) connected to one CPU.

Display part 26 displays the computation results of computation part 25 along with error messages and operating procedures for example, and may include for example a liquid crystal display device.

Next, the procedures for measuring the blood sugar concentration using biosensor 1 and concentration measuring system 2 are explained.

As clearly shown in FIG. 5, biosensor 1 is first set on concentration measuring system 2. Terminals 31b and 32b of working electrode 31 and counter electrode 32 of biosensor 1 are thus connected to first and second terminals 20a and 20b of concentration measuring system 2. This allows voltage to be applied between working electrode 31 and counter electrode 32 via first and second terminals 20a and 20b. Under actual measurement conditions, a constant voltage is applied between working electrode 31 and counter electrode 32 as soon as biosensor 1 is mounted on concentration measuring system 2. The constant voltage applied between working electrode 31 and counter electrode 32 is set for example in the range of 100 to 1000 mV. In this embodiment, application of the constant voltage between working electrode 31 and counter electrode 32 is performed continuously until the response current for computing the blood sugar concentration has been measured.

Figure 4A:
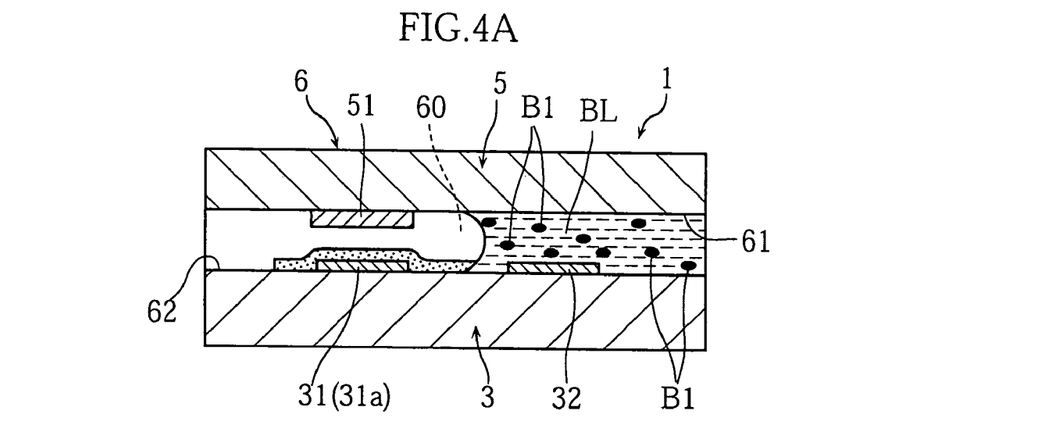
FIGS. 4A and 4B are cross-sections as in FIG. 3 for explaining the flow of blood through the interior channel of the biosensor.
Figure 4B:
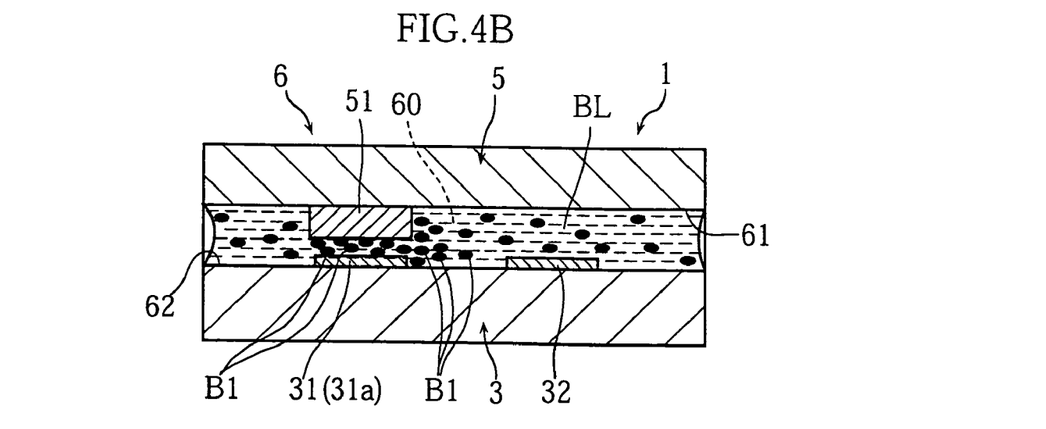

Next, blood is supplied via end opening 61 of biosensor 1. As shown in FIGS. 4A and 4B, blood BL travels by capillary action through internal channel 60 from end opening 61 to end opening 62 of capillary 6. As clearly shown in FIG. 4B, blood BL is introduced until blood BL reaches end opening 62 and internal channel 60 of capillary 6 is full of blood BL. In this process reagent site 33 (see FIG. 4A) is dissolved by blood BL and a liquid reaction system is formed in internal channel 60. At this time water-absorbing layer 51 absorbs the plasma component of blood BL, and water-absorbing layer 51 grows in thickness. In this way, the movement of blood cells B1 is impeded by water-absorbing layer 51, and the concentration of blood cells B1 rises on and around the surface of electron transfer interface 31a of working electrode 31.

Within the liquid reaction system, the glucose in blood BL is oxidized by oxidoreductase while the electron transporter becomes reduced. When a voltage is applied, the reduced electron transporter moves to the surface of electron transfer interface 31a of working electrode 31, supplies electrons to electron transfer interface 31a and reverts to an oxidized electron transporter. The amount of electrons supplied to electron transfer interface 31a is measured as a response current by current measuring part 22 via first and second terminals 20a and 20b.

Meanwhile, the response current measured by current measuring part 22 is monitored by detection part 23, and once the response current exceeds a threshold detection part 23 detects that the blood has been supplied to reagent part 33 and reagent part 33 has dissolved. When detection part 23 has detected that the blood has been supplied, detection part 23 then evaluates whether a fixed time has passed since this detection.

When detection part 23 has determined that a fixed time has passed, a response current is measured at current measuring part 22 and the blood sugar concentration is computed by computing part 25 based on the response current. Computation of the blood sugar concentration is performed by first converting the response current to a voltage and then comparing the voltage to a previously-prepared reference curve showing the relationship between voltage values and blood sugar concentrations. The computation result of computation part 25 is displayed on display part 26 for example.

In this embodiment, when blood BL is supplied to internal channel 60 of capillary 6 the plasma component of blood BL is absorbed by water-absorbing layer 51, increasing the concentration of blood cells B1 on and around the surface of electron transfer interface 31a of working electrode 31. In this way, the area on and around the surface of electron transfer interface 31a is artificially in the same state as if high-hematocrit blood BL were being supplied. Moreover, if an absorbent polymer material with a water absorption power of 10 to 500 g/g is used, water-absorbing layer 51 will absorb more plasma the lower the hematocrit value of blood BL. As a result, a similar high hematocrit state can be achieved around water-absorbing layer 51 regardless of whether the hematocrit value is high or low.

Biosensor 1 can also resolve issues involved in separating blood cells from blood in the measuring instrument. That is, in methods of separating blood cells the plasma component has to be passed through a separation membrane, prolonging the measurement time and reducing the amount of blood that can be used in the reaction relative to the amount supplied. In contrast, because in biosensor 1 there is no separation membrane or other obstruction to the progress of blood BL through internal channel 60 of capillary 6, measurement time is not prolonged as it is with a separation membrane. Moreover, because in biosensor 1 most of the blood BL supplied to internal channel 60 of capillary 6 can be reacted with oxidoreductase of reagent part 33, concentrations can be measured properly using only a tiny amount of blood BL.

Next, a biosensor according to the second embodiment of the present invention is explained with reference to FIG. 6.

Figure 6:
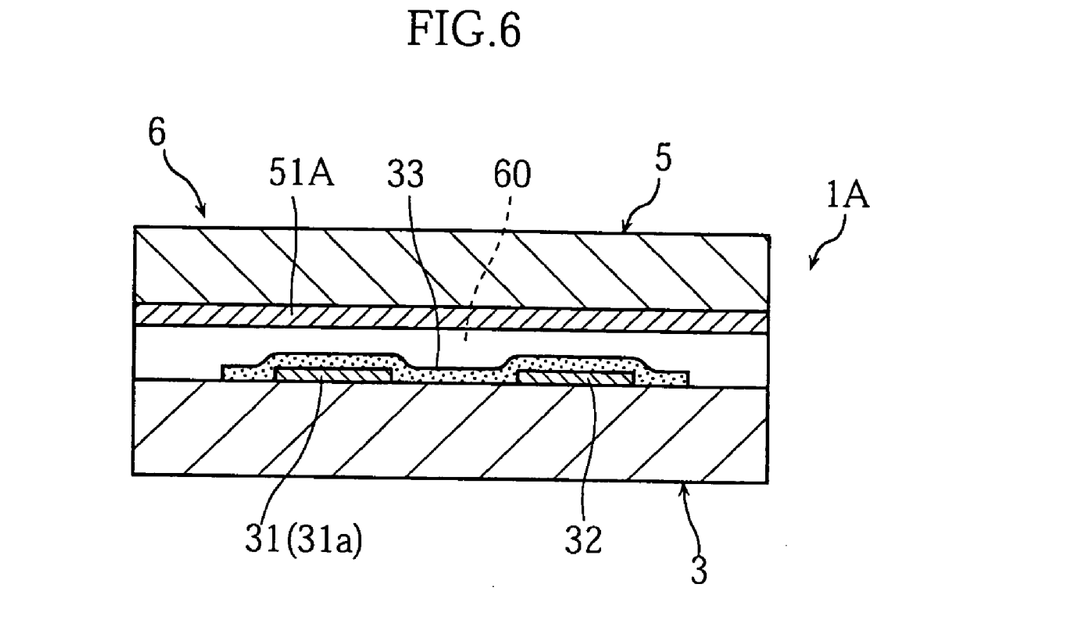
FIG. 6 is a cross-section showing a biosensor according to a second embodiment of the present invention.

In the biosensor 1A shown in FIG. 6, water-absorbing layer 51A is formed across the entire length of capillary 6. This water-absorbing layer 51A can be formed for example by affixing a water-absorbing sheet of an absorbent polymer material to the cover. Water-absorbing layer 51A can also be formed by coating the cover with a solution of an absorbent polymer material dissolved together with an adhesive component in a solvent, and then drying the coat.

An absorbent layer can also be formed across the entire length of capillary 6 by making all of cover 5 water absorbent and having all of cover 5 comprise the water-absorbing layer. Such a water-absorbing layer (cover) can be formed for example by first mixing an absorbent polymer material with a resin material to make a molding material which is then subjected to resin molding.

Next, a biosensor according to the third embodiment of the present invention is explained with reference to FIG. 7.

Figure 7:
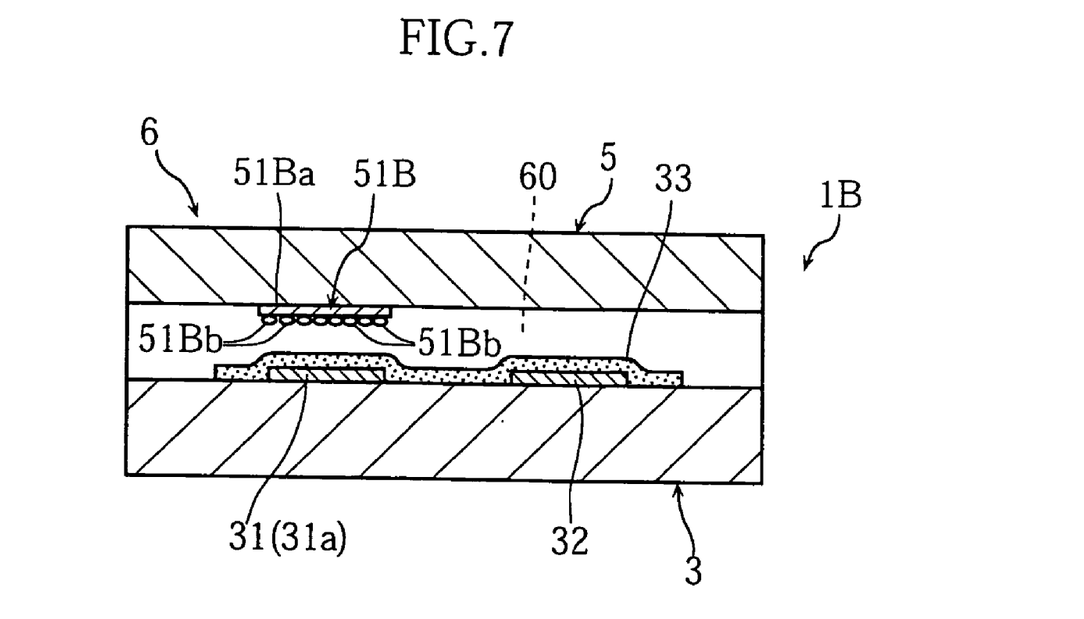
FIG. 7 is a cross-section showing a biosensor according to a third embodiment of the present invention.

The biosensor 1B shown in FIG. 7 includes water-absorbing layer 51B having absorbent polymer grains. This water-absorbing layer 51B, in which absorbent polymer grains 51Bb are held on one side of double-sided tape 51Ba, is affixed to the cover using the adhesiveness of the other side of the double-sided tape. An absorbent polymer with a weight-average grain size of 100 to 1000 μm may be preferably used.

Next, a biosensor according to the fourth embodiment of the present invention is explained with reference to FIGS. 8A and 8B.

Figure 8A:
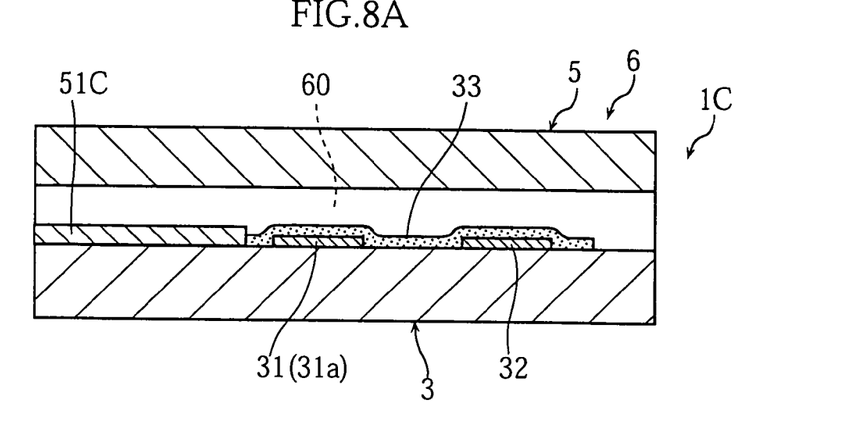
FIGS. 8A and 8B are cross-sections showing a biosensor according to a fourth embodiment of the present invention.

In the biosensor 1C shown in FIG. 8A, water-absorbing layer 51C is formed on substrate 3 downstream in the direction of blood flow from electron transfer interface 31a of working electrode 31. However, water-absorbing layer 51C may also be formed on cover 5.

Figure 8B:
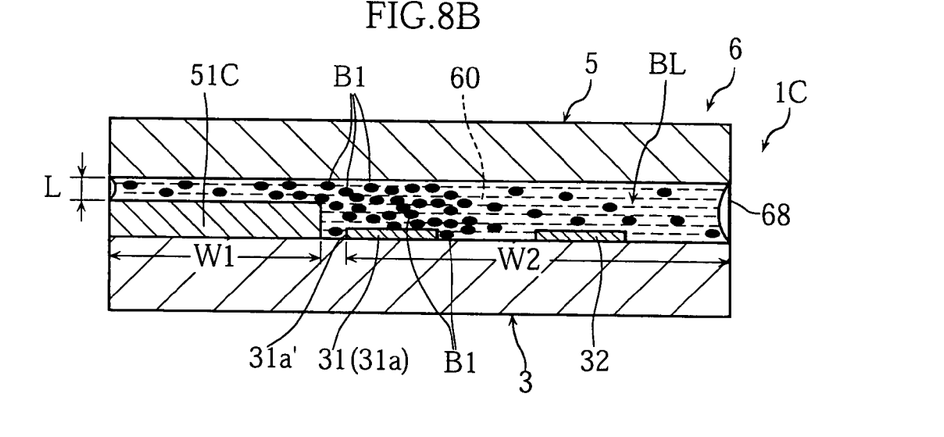

In this biosensor 1C, as shown in FIG. 8B, when blood BL is introduced into capillary 6 water-absorbing layer 51C expands, decreasing the spatial cross-sectional area of the part of capillary 6 having formed water-absorbing layer 51C. As a result, the movement of blood cells B1 is impeded by water-absorbing layer 51C, blood cells B1 accumulate near electron transfer interface 31a and the concentration of blood cells B1 increases around electron transfer interface 31a.

In order for this to be effective, water-absorbing layer 51C is preferably formed so that the distance L between water-absorbing layer 51C and the upper surface of the capillary is 0 to 15 μm when capillary 6 is filled with blood. Moreover, in order to more reliably increase the concentration of blood cells B1 around electron transfer interface 31a it is desirable that dimension W1 of water-absorbing layer 51C in the direction of flow of blood BL be made relatively large. Dimension W1 in this case is preferably set to about ¼ to ½ of the distance W2 between inlet 68 of capillary 6 and downstream end 31a' of electron transfer interface 31a.

A function similar to that of the water-absorbing layer 51C shown in FIGS. 8A and 8B can be achieved with a non-(or low-) water-soluble dam part. That is, rather than causing blood cells to accumulate due to absorption of the plasma component and expansion, the cross-sectional dimensions downstream from electron transfer interface 31a in capillary 6 can be made small by the formation of a dam before blood is supplied. This dam is preferably formed so that the distance (corresponding to L in FIG. 8B) between the dam and the substrate (or cover) is 5 to 15 μm. The dam can be formed on either the substrate or the cover.

Next, a biosensor according to the fifth embodiment of the present invention is explained with reference to FIGS. 9, 10A and 10B.

Figure 9:
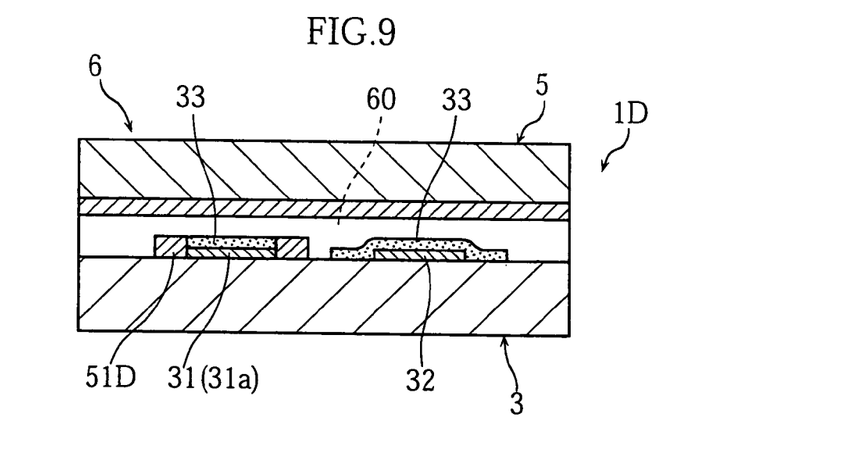
FIG. 9 is a cross-section showing a biosensor according to a fifth embodiment of the present invention.
Figure 10A:
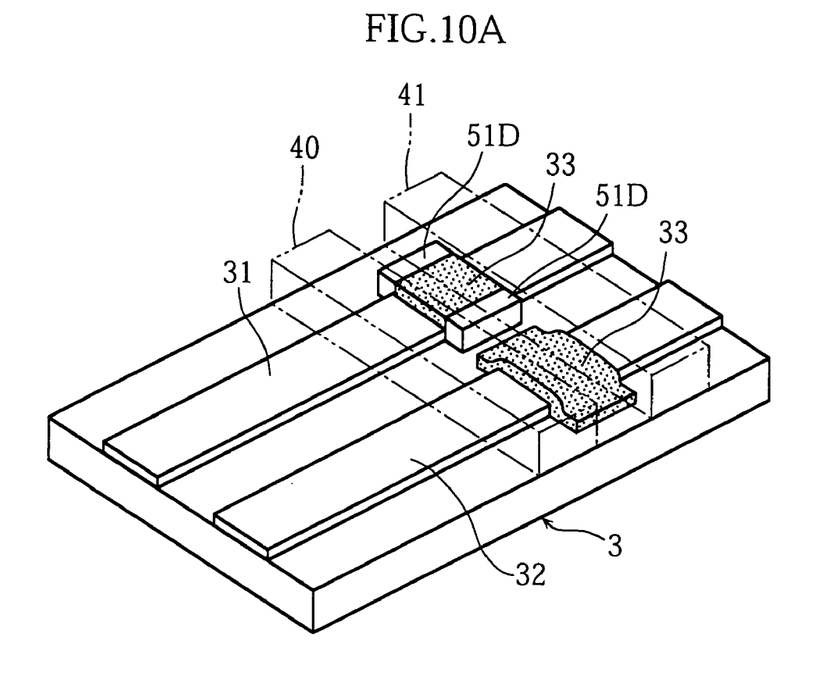
FIGS. 10A and 10B are perspective views showing the biosensor of FIG. 9 with the cover and spacers removed.
Figure 10B:
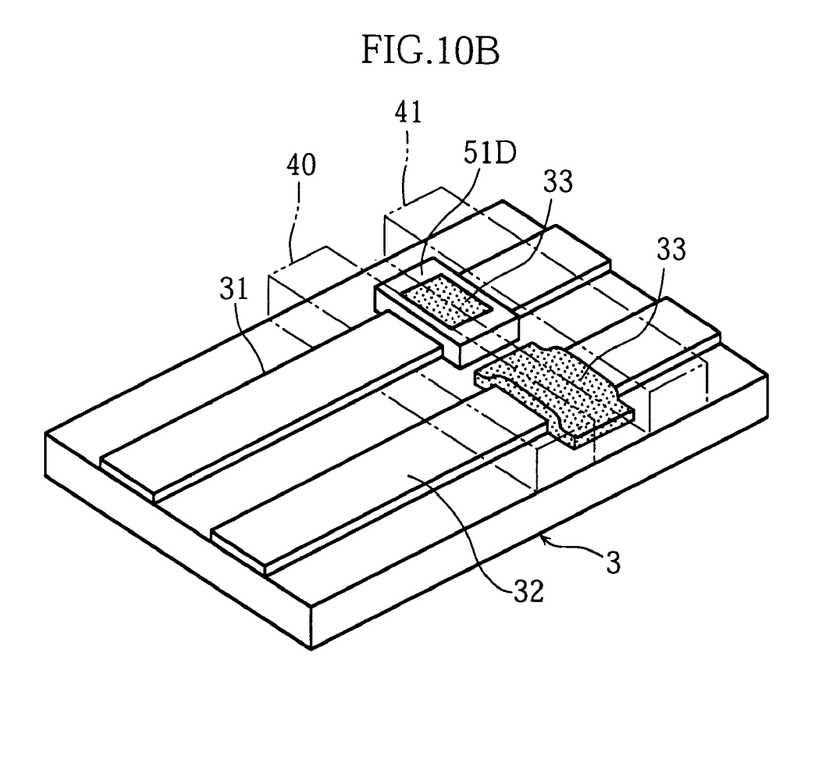

In the biosensor 1D shown in FIG. 9, water-absorbing layer 51D is formed so as to have a part adjoining electron transfer interface 31a of working electrode 31. As shown in FIG. 10A, water-absorbing layer 51D may be arranged in two sites both upstream and downstream from electron transfer interface 31a (see FIG. 9), or as shown in FIG. 10B it can be formed as a rectangular frame. In the configuration shown in FIG. 10A, one of the two water-absorbing layers 51D may also be omitted.

The measurement of blood glucose concentration was taken as an example in the above explanation, but the present invention is applicable to measurement of other components in blood such as cholesterol, lactic acid, bilirubin and the like, as well as to sample liquids other than blood.

EXAMPLES

It is shown below that the effect of blood cells in blood on measurement of response current is reduced by the biosensor of the present invention.

Example 1

(Preparation of Glucose Sensor)

In this example, a biosensor was formed with the same structure as in FIGS. 1 through 4. In this biosensor, the length L, width W and height H of internal channel 60 of capillary 6 were given as 3 mm, 1 mm and 40 μm, respectively (see FIGS. 1 and 3). Working electrode 31 and counter electrode 32 were formed by screen printing using carbon ink (Japan Acheson "Electrodag 423SS"). Reagent site 33 was given a two-layer structure consisting of an electron transport layer and an enzyme-containing layer. The electron transport layer was formed by first applying 0.4 μL of a first material liquid comprising an electron transporter to substrate 3, and then blow drying (30° C., 10% Rh) the first material liquid. The enzyme-containing layer was formed by first applying 0.3 μL of a second material liquid containing oxidoreductase to the electron transport layer, and then blow drying (30° C., 10% Rh) the second material liquid.

The first material liquid was prepared by mixing the liquid components in the following table 1 in numerical order from 1 to 4, letting the mixture stay for 1 to 3 days and then adding an electron transporter thereto. The second material liquid was prepared by dissolving an oxidoreductase in 0.1% CHAPS.

$[Ru(NH_3)_6]Cl_3$ (Dojin Chemical Laboratory "LM722") was used as the electron transporter, and PGGGDH (800 U/mg glucose dehydrogenation activity) was used as the oxidoreductase.

| (1) SWN Solution | | (2) CHAPS Solution | | (3) Distilled water | (4) ACES Solution | |
|---|---|---|---|---|---|---|
| Concentration | Content | Concentration | Content | | Concentration | Content |
| 1.2% | 250 μL | 10% | 25 μL | 225 μL | 200 mM | 500 μL |

In Table 1, SWN is an abbreviation for Lucentite SWN, CHAPS is an abbreviation for 3-[(3-cholamidopropyl)dimethylammonio]propanesulfonic acid, and ACES is an abbreviation for N-(2-acetamido)-2-aminoethanesulfonic acid. Coop Chemical "3150" was used as the SWN, Dojin Chemical Laboratory "KC062" as the CHAPS and Dojin chemical Laboratory "ED067" as the ACES. The ACES solution was adjusted to a pH of 7.5.

Water-absorbing layer 51 was formed to a thickness of 2 μm by first applying 0.1 μL of a coating material comprising an absorbent polymer to the target site of cover 5 and then blow drying it (30° C., 10% Rh). 7 parts by weight of absorbent polymer (Sumitomo "Aquacork") dissolved in 100 parts by weight of methanol was used as the coating material.

(Measuring Response Current)

Figure 11:
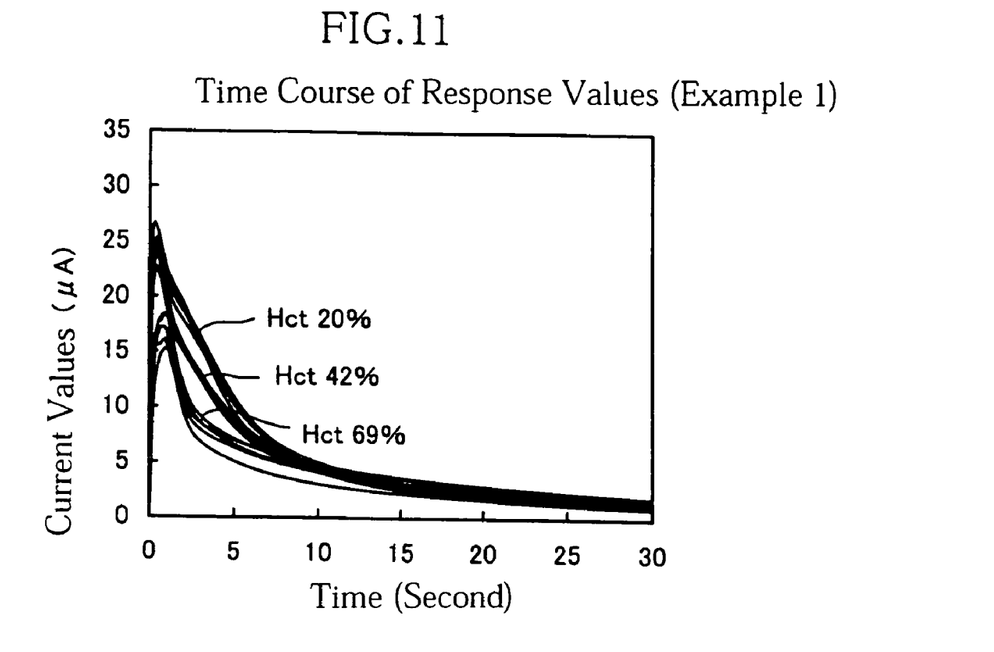
FIG. 11 is a graph of the time course of response current in the biosensor of Example 1.

Using the biosensor described above, response current was measured as a time course for three types of blood (Hct 20%, Hct 42% and Hct 69%) with different hematocrit (Hct) values and a glucose concentration of 447 mg/dL. Response current was measured 5 times for each Hct type of blood. The amount of blood supplied to internal channel 60 of biosensor 1 here was 0.5 μL, and the voltage applied between working electrode 31 and counter electrode 32 was 500 mV. The results are shown in FIG. 11.

Figure 13:
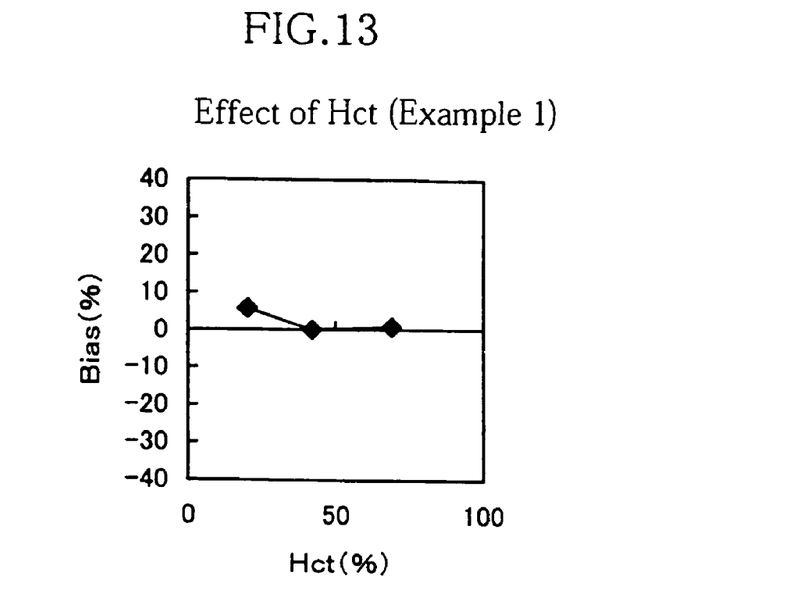
FIG. 13 is a graph showing the effect of hematocrit (Hct) in the biosensor of Example 1.

The effect of Hct was investigated based on response current 5 seconds after the supply of blood. The results are shown in FIG. 13. In FIG. 13 Hct (%) is shown on the horizontal axis and percent bias from response current at Hct 42% on the vertical axis. In FIG. 13, percent bias is shown as the average of 5 measurements.

Comparative Example 1

Figure 12:
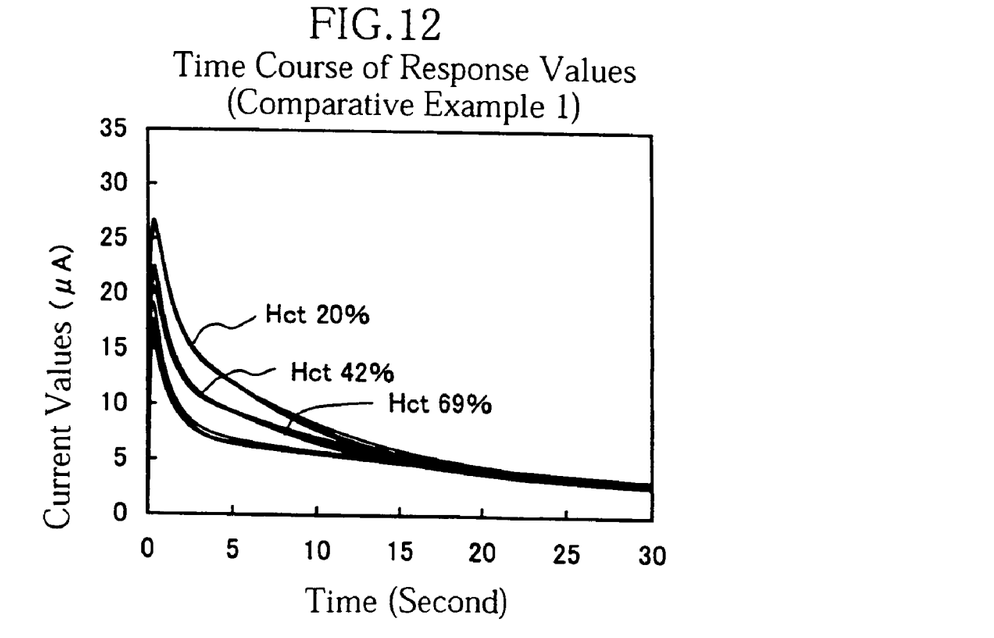
FIG. 12 is a graph of the time course of response current in the biosensor of Comparative Example 1.
Figure 14:
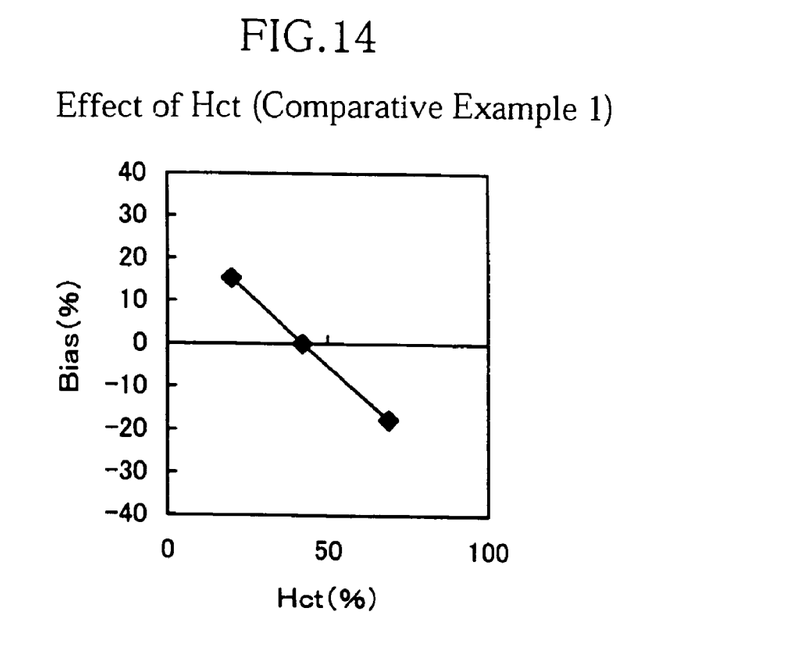
FIG. 14 is a graph showing the effect of hematocrit (Hct) in the biosensor of Comparative Example 1.

In this comparative example a biosensor was used having the absorbent layer omitted from the biosensor of Example 1, and a time course of response current was measured for three types of blood of differing Hct as in Example 1. Response current was measured 5 times for each Hct type of blood. The results are shown in FIG. 12. Also as in Example 1, the effect of Hct was investigated based on response current 5 seconds after beginning blood supply. The results are shown in FIG. 14.

Discussion of Experimental Results

As can be seen from FIGS. 11 and 12, the response current tended to converge more quickly with the biosensor of Example 1 than with the biosensor of Comparative Example 1 when blood of different Hct was measured. First, as can be understood from looking at the 5-second values for response current for example, the difference in response current between Hct 20% and Hct 69% was smaller with the biosensor of Example 1 than with the biosensor of Comparative Example 1, and second, the response current for each sample had become uniform after about 8 seconds with the biosensor of Example 1. With the biosensor of Comparative Example 1, by contrast, it took about 15 seconds for the response current to become uniform.

These results mean that the biosensor of Example 1 is capable of performing proper concentration measurement in less time than the biosensor of Comparative Example 1. Moreover, because in the biosensors of Example 1 and Comparative Example 1 the internal channel 60 of capillary 6 has a small volume of 0.5 μL, it appears that the biosensor of Example 1 can precisely measure tiny quantities of blood.

Although reproducibility is less with the biosensor of Example 1 than with the biosensor of Comparative Example 1, this is probably attributable to variation in the formation of water-absorbing layer 51 because the coating material was applied by hand to form water-absorbing layer 51. Consequently, reproducibility could probably be improved if water-absorbing layer 51 could be formed uniformly.

As can be seen from FIGS. 13 and 14, the biosensor of Example 1 had a bias of +5% in response current 5 seconds after initiation of blood supply within the range of Hct 20–69%, while the biosensor of Comparative Example 1 had a bias of ±20%. This means that in the biosensor of Example 1 Hct affects response current less than it does in the biosensor of Comparative Example 1. These results show that the effect of blood Hct is reduced by the inclusion of a water-absorbing layer 51 such as that of the biosensor in Example 1.

As explained above, with the measuring instrument of the present invention it is possible to precisely measure concentration in a small quantity of sample liquid while controlling the effect of the solid components in the sample liquid and keeping the measurement time short.

The invention claimed is:

1. A measuring instrument comprising:
    a channel comprising a sample inlet opening and an exhaust opening,
    the channel allows for moving a sample liquid containing a solid component from the sample inlet opening toward the exhaust opening and for providing a liquid reaction field;
    a first electrode and a second electrode which are used to apply voltage to the liquid reaction field,
    wherein a distance from the sample inlet opening to the first electrode is greater than a distance from the sample inlet opening to the second electrode,
    wherein the first electrode comprises an electron transfer interface for providing electrons to the liquid reaction field or receiving electrons from the reaction field when voltage is applied to the liquid reaction field via the first and second electrodes;
    a concentration means for increasing the concentration of the solid component in a part in which solid component contacts the electron transfer interface in the liquid reaction field; and
    a water-absorbing layer positioned only downstream from the second electrode in a flow direction of the sample liquid,
    wherein the water-absorbing layer allows flow of the sample liquid from the sample inlet opening toward the second electrode but restricts flow of the sample liquid from the first electrode toward the exhaust opening.

2. The measuring instrument according to claim 1, wherein the water-absorbing layer contains an absorbent polymer material.

3. The measuring instrument according to claim 2, wherein the absorbent polymer material has water absorption power of 10 to 500 g/g.

4. The measuring instrument according to claim 2, further comprising a substrate on which the first and the second electrodes are positioned, and a cover above the substrate.

5. The measuring instrument according to claim 4, wherein the water-absorbing layer is formed as a film on at least that part of the cover which faces the electron transfer interface.

6. The measuring instrument according to claim 5, wherein the water-absorbing layer without water absorption and with water absorption has thicknesses of 1/30 to 1/10 and 1/5 to 3/5, respectively, relative to a depth of the channel.

7. The measuring instrument according to claim 4, wherein the water-absorbing layer comprises a powder of the absorbent polymer material is supported on the cover.

8. The measuring instrument according to claim 7, wherein the powder has a weight average grain size of 100 to 1000 μm without water absorption.

9. The measuring instrument according to claim 2, wherein the water-absorbing layer is provided downstream in a flow direction of the sample liquid from the electron transfer interface in the channel.

10. The measuring instrument according to claim 9, wherein the water-absorbing layer has a relative length in the flow direction of the sample liquid is 1/4 to 1/2 of a distance from the sample inlet opening of the channel to a furthest downstream point of the electron transfer interface in the flow direction of the sample fluid.

11. The measuring instrument according to claim 9, wherein the water-absorbing layer is formed so that a portion of the channel in which the water-absorbing layer with water absorption is spaced from the cover by 0 to 15 μm.

12. The measuring instrument according to claim 4, wherein at least a portion of the water-absorbing layer has a part positioned either upstream from or downstream from the electron transfer interface while also being positioned adjacent to the electron transfer interface.

13. The measuring instrument according to claim 12, wherein the water-absorbing layer comprises a part positioned upstream from and adjacent to the electron transfer interface, and another part positioned downstream from and adjacent to the electron transfer interface.

14. The measuring instrument according to claim 13, wherein the water-absorbing layer surrounds the electron transfer layer.

15. The measuring instrument according to claim 1, wherein the sample liquid is blood containing blood cells.

16. A measuring instrument comprising:
a channel for moving a sample liquid containing a solid component and for providing a liquid reaction field, and
first and second electrodes which are used to apply voltage to the liquid reaction field,
wherein the first electrode comprises an electron transfer interface for providing electrons to the liquid reaction field or receiving electrons from the reaction field when voltage is applied to the liquid reaction field via the first and second electrodes, the measuring instrument comprising concentration means for increasing the concentration of the solid component in a part which contacts the electron transfer interface in the liquid reaction field;
wherein the concentration means comprises a water-absorbing layer containing an absorbent polymer material; and
wherein the absorbent polymer material has a water absorption power of 10 to 500 g/g.

* * * * *